United States Patent
Baniameri et al.

(10) Patent No.: US 9,886,547 B2
(45) Date of Patent: Feb. 6, 2018

(54) METHOD AND SYSTEM FOR AUTOMATED HEALTHCARE CARE COORDINATION AND CARE TRANSITIONS

(71) Applicant: Health Business Intelligence Corp., Scottsdale, AZ (US)

(72) Inventors: Siamak Baniameri, Chandler, AZ (US); Koorosh Yasami, Scottsdale, AZ (US); Greg Wong, Mesa, AZ (US)

(73) Assignee: Health Business Intelligence Corp., Scottsdale, AZ (US)

( * ) Notice: Subject to any disclaimer, the term of this patent is extended or adjusted under 35 U.S.C. 154(b) by 336 days.

(21) Appl. No.: 13/949,461

(22) Filed: Jul. 24, 2013

(65) Prior Publication Data

US 2014/0278480 A1    Sep. 18, 2014

Related U.S. Application Data

(60) Provisional application No. 61/801,309, filed on Mar. 15, 2013.

(51) Int. Cl.
*G06F 19/00* (2011.01)

(52) U.S. Cl.
CPC ......... *G06F 19/322* (2013.01); *G06F 19/327* (2013.01)

(58) Field of Classification Search
None
See application file for complete search history.

(56) References Cited

U.S. PATENT DOCUMENTS

| | | | |
|---|---|---|---|
| 2006/0235280 A1* | 10/2006 | Vonk et al. | 600/300 |
| 2009/0265185 A1* | 10/2009 | Finn et al. | 705/3 |
| 2011/0131060 A1* | 6/2011 | Schuster | G06Q 10/10 705/3 |

* cited by examiner

*Primary Examiner* — Linh Giang Le
(74) *Attorney, Agent, or Firm* — Snell & Wilmer L.L.P.

(57) ABSTRACT

A system and method configured for coordinating healthcare services is disclosed. The method can comprise selecting a patient for care coordination based in part on a patient diagnosis and data analytics, assigning a predetermined patient care flow plan to a patient based in part on the patient diagnosis, modifying the predetermined patient care flow plan in response to input from at least one of a healthcare provider and the patient, and generating a customized patient care flow plan for the patient, executing the customized care flow, and engaging the patient by providing to the patient at least one of patient scheduling, notifications, a personal health record, patient home monitoring, and patient education and medication information materials. The present disclosure further includes computer program product of a computer-readable medium usable with a programmable computer and having computer-readable code embodied therein for coordinating healthcare services.

12 Claims, 14 Drawing Sheets

Census  _Dashboard_  Scheduling  Secure Messaging  Care Plans  Profile

| NAME | DOB | SSN | CARE PLAN | PROVIDER | LAST STEP | CURRENT STEP | NEXT STEP |
|---|---|---|---|---|---|---|---|
| John Doe | 12/18/1912 | 555-55-5555 | R/R | Jane Doe | Request Patient APPTs 11/15/2012 ✓ | APPT Requests Sent 11/16/2012 ✓ | Schedule MED Reminders 11/17/2012 ✗ |
| Jack Black | 12/18/1912 | 444-44-4444 | C/C | Jack Black | Request Patient APPTs 11/15/2012 ✓ | APPT Requests Sent 11/16/2012 ✓ | Schedule MED Reminders 11/17/2012 ✗ |
| John Doe | 12/18/1912 | 555-55-5555 | R/R | Jane Doe | Request Patient APPTs 11/15/2012 ✓ | APPT Requests Sent 11/16/2012 ✓ | Schedule MED Reminders 11/17/2012 ✗ |

FIGURE 2

*Census    Dashboard    Scheduling    Secure Messaging    Care Plans    Profile*

Title: [____]    Created by: [____]    Start Date: [____]

Send Patient EDU
MED Reminder Sent
MED Reminder Response
Patient EDU Sent
Monitoring Messages Sent
Monitoring Response
APPTs Scheduled
APPT Notification Sent
APPT Notification Response
APPT Reminder Sent
APPT Reminder Response
Send Discharge Summary
APPT Follow-up Sent
APPT Follow-up response
Request Visit Summary
Visit Summary Received
Export Visit Summary
Patient Inactive Request Patient APPTs
APPT Requests Sent
Schedule MED Reminders
Schedule Patient Monitoring

ADD▶
◀REMOVE

SUBMIT

FIGURE 6

Care Coordination Workflow Example

| | |
|---|---|
| 1 | ER Visit/Discharge Notifications to PCP |
| 2 | Send Discharge Summaries to Providers |
| 3 | Request Appointments From Providers |
| 4 | Send Patient Education Materials |
| 5 | Perform Medication Assessment |
| 6 | Send Patient Medication Reminders |
| 7 | Analyze Results/Notify if Needed |
| 8 | Send Patient Monitoring Messages |
| 9 | Analyze Results/Notify if Needed |
| 10 | Send Patient Appointment Notifications |
| 11 | Analyze Response/Reschedule if Needed |
| 12 | Send Patient Appointment Reminders |
| 13 | Analyze Response/Reschedule if Needed |
| 14 | Send Patient Appointment Follow ups |
| 15 | Analyze Results/Follow up if Needed |
| 16 | Request Visit Summaries From Providers |
| 17 | Manage Patient PHR |

METHOD AND SYSTEM FOR AUTOMATED HEALTHCARE CARE COORDINATION AND CARE TRANSITIONS

PRIORITY CLAIM

This application is a non-provisional of, and claims the benefit of, U.S. Provisional Application No. 61/801,309, entitled, "METHOD AND SYSTEM FOR AUTOMATED HEALTHCARE CARE COORDINATION AND CARE TRANSITIONS," which was filed on Mar. 15, 2013, which is hereby incorporated by reference for any purpose in its entirety.

FIELD OF THE DISCLOSURE

The present disclosure relates to the field of coordinating patient healthcare services, and in particular, relates to coordinating patient healthcare services amongst multiple healthcare providers.

BACKGROUND ART

Studies have shown that elderly patients with one of six major chronic diseases create the highest costs for Medicare and private health insurance companies from hospital admissions and readmissions. The major contributing factor for this out-of-control spending is the lack of community or ambulatory care coordination. Once patients with chronic diseases are discharged from hospitals, they enter a fragmented and reactive clinical model that does neither engage nor support them throughout the continuum of care. This fragmented system keeps patients and healthcare providers disconnected and out of sync, creating confusion for patients and misinformation and inefficiency for healthcare providers. Patients with chronic diseases are often left unattended, uninformed and in total disconnect from community care. Typically, due to time restraints, declining reimbursements, and lack of resources, the healthcare system waits until the patient reaches a critical point and use the ER as patient's re-entry into the health care system.

SUMMARY

The present disclosure provides a method, computer-readable medium and system for coordinating healthcare services. In various embodiments, a care coordination system can comprise a patient selection module configured to select a patient for care coordination based in part on a patient diagnosis and data analytics, a care coordination module configured to assign a predetermined patient care flow plan to the patient based in part on the patient diagnosis, a patient engagement module configured to engage the patient by providing to the patient at least one of patient scheduling, notifications, a personal health record, patient home monitoring, and patient education and medication information materials, and a communication gateway module configure to receive information from the patient and the healthcare provider. The care coordination module can be configured to modify the predetermined patient care flow plan in response to input from at least one of a healthcare provider and the patient in order to generate a customized patient care flow plan for the patient. The care coordination system can further comprise an authorization module configured to authorize control of the customized patient care flow plan to a first healthcare provider for care coordination, and the authorization module can be further configured to transition control of the patient care plan to a second healthcare provider for care coordination.

The disclosure also provides an exemplary method of coordinating healthcare services. The method can comprise selecting a patient for care coordination based in part on a patient diagnosis and data analytics, assigning a predetermined patient care flow plan to a patient based in part on the patient diagnosis, modifying the predetermined patient care flow plan in response to input from at least one of a healthcare provider and the patient, and generating a customized patient care flow plan for the patient, executing the customized care flow, and engaging the patient by providing to the patient at least one of patient scheduling, notifications, a personal health record, patient home monitoring, and patient education and medication information materials. The present disclosure further includes computer program product of a computer-readable medium usable with a programmable computer and having computer-readable code embodied therein for coordinating healthcare services.

BRIEF DESCRIPTION OF THE DRAWINGS

FIG. 2 illustrates a screen shot of a care coordination dashboard, in accordance with various embodiments;

FIG. 6 illustrates a screen shot of customizable patient care plan generation, in accordance with various embodiments;

FIGS. 7A-B illustrate exemplary patient care plan workflows, in accordance with various embodiments;

FIG. 9 illustrates a screen shot of a medication reminder, in accordance with various embodiments;

DETAILED DESCRIPTION

Figure 1A:
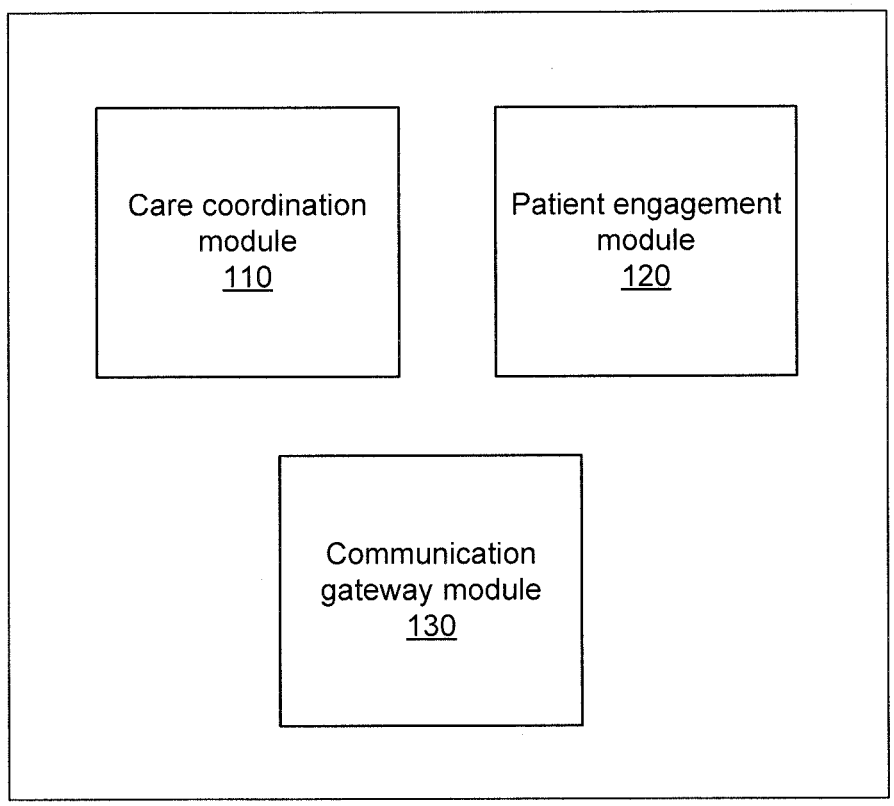
FIGS. 1A-B illustrate exemplary care coordination systems, in accordance with various embodiments.

Various embodiments presented herein relate to actively coordinating and transitioning chronically ill patients from hospital discharge to their primary care and specialty care appointments. The coordinated effort, also known as navigation, can be extremely successful in preventing hospital admissions and readmissions for patients with chronic disease. Often times, severely ill patients are overwhelmed or just confused with their post discharge instructions. The act of reminding or explaining the appointment schedule to these sick patients, providing education, making additional appointments, and/or various reminders can be the difference in successful follow up care. Active care coordination can reduce hospital admissions and readmissions. Studies show that patients with six major chronic diseases utilize the greatest amount of Medicare's Financial Resources. Due to the lack of patient education, prevention, coordinated care, information sharing and monitoring, these patients tend to spend a good deal of time in and out of hospitals. It is estimated that Medicare spends 70% of its budget on managing care for patients with chronic diseases. The six identified diagnosis include: chronic obstructive pulmonary disease (COPD), asthma, diabetes, pneumonia, Congestive heart failure (CHF), and depression. By reducing hospital admission and readmission of this patient population, Medicare can reduce costs drastically.

The detailed description of exemplary embodiments herein makes reference to the accompanying drawings and figures, which show the exemplary embodiments by way of illustration only. While these exemplary embodiments are described in sufficient detail to enable those skilled in the art to practice the present disclosure, it should be understood that other embodiments may be realized and that logical and mechanical changes may be made without departing from the spirit and scope of the present disclosure. It will be apparent to a person skilled in the pertinent art that this disclosure can also be employed in a variety of other applications. Thus, the detailed description herein is presented for purposes of illustration only and not of limitation. For example, the steps recited in any of the method or process descriptions may be executed in any order and are not limited to the order presented.

The present disclosure is described herein with reference to system architecture, block diagrams and flowchart illustrations of methods, and computer program products according to various aspects of the present disclosure. It will be understood that each functional block of the block diagrams and the flowchart illustrations, and combinations of functional blocks in the block diagrams and flowchart illustrations, respectively, can be implemented by computer program instructions.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flow diagram illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions.

The present disclosure is now described in terms of an exemplary system in which the present disclosure, in various embodiments, would be implemented. This is for convenience only and is not intended to limit the application of the present disclosure. It will be apparent to one skilled in the relevant art(s) how to implement the present disclosure in alternative embodiments.

Figure 1B:
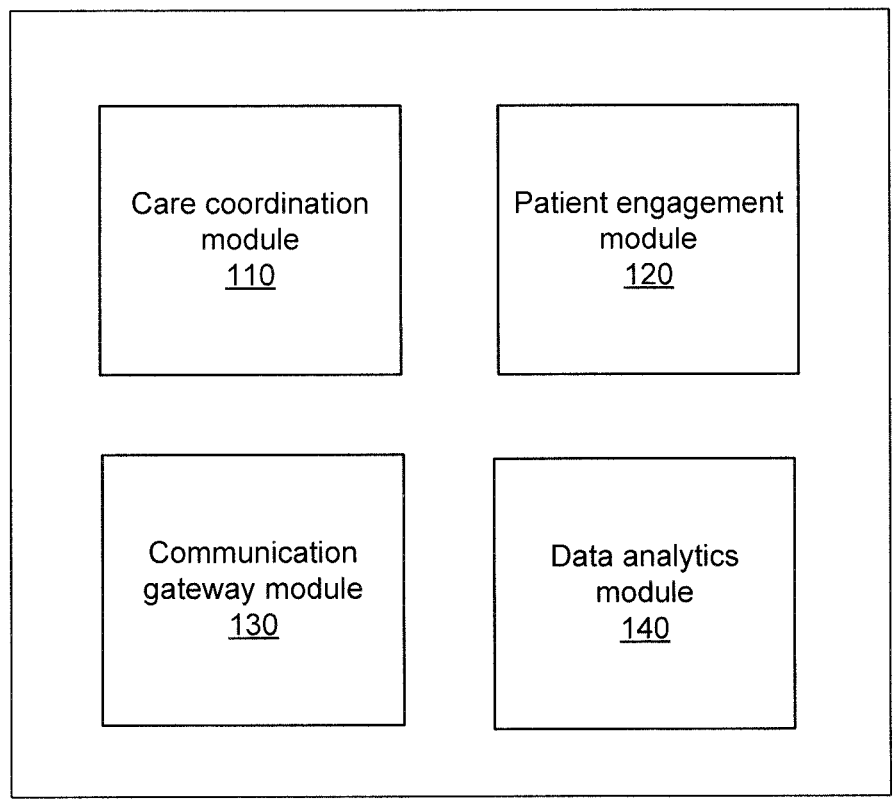

In accordance with various embodiments and with reference to FIG. 1A, a care coordination system 100 comprises a care coordination module 110, a patient engagement module 120, and a communication gateway module 130. Furthermore, in various embodiments, care coordination system 100 can also comprise a data analytics module 140, as shown in FIG. 1B. Each module can be configured for various functionalities to manage the process flow of patient care, and address aspects of care coordination, care transition, and patient engagement. For example, care coordination system 100 can manage the patient coordination by facilitating secure communication, appointment scheduling, patient appointment notifications, reminders and follow-ups, patient home monitoring, monitoring data analytics, medication notification, information regarding support groups, providing patient education, alert notifications, electronic referrals, patient outreach, readmission reductions, medical record exchanges, and any combination therefore. The example capabilities are intended to convey the potential scope of the care coordination and care transition system and are not essential or limiting to the system. In accordance with various embodiments, care coordination system 100 can be implemented in a software as a service (SaaS) environment.

Care coordination module 110 can be configured for active coordination and transition of patient healthcare between multiple healthcare providers. In various embodiments, care coordination module 110 can include a care coordination dashboard. An exemplary screenshot of the care coordination dashboard is illustrated in FIG. 2. The care coordination dashboard can enable care coordinators to keep track of all events during the course of patient engagement. Care coordination module 110 can keep track of all events that take place during the care coordination period, automatically update patient progress, and initiate next steps in the patient care plan. The dashboard can enable a care coordinator to visually see the patient care plan progress or the lack thereof. The care coordination dashboard can simplify the entire process of care coordination and patient engagement. At a glance, the care coordinator is capable of viewing the progress and visually seeing where the patient is on the spectrum of care. Patient care coordinators, such as case management workers, can effectively monitor the transitional ambulatory care of post-discharge patients.

In various embodiments, care coordination module 110 can be configured for customized patient care flow plans for patient transitional care. For example, in various embodiments, care coordination module 110 can generate executable predetermined patient care flow plans assigned to particular disease states, as will be discussed herein. Furthermore, in various embodiments, care coordination module 110 can interface with communication gateway module 130 to assess patient engagement in the patient care flow plan. Moreover, in various embodiments, care coordination module 110 can be configured to manage transition of care among healthcare providers.

Patient engagement module 120 can be configured for patient engagement. In various embodiments, patient engagement module 120 can be configured to manage scheduling, monitoring, and sending notifications and reminders of appointments and medication. In various embodiments, patient engagement module 120 can be configured to allow care coordinators to send alert notifications to a large number of patients at once. These alert notifications can include the availability of support group meetings, certain vaccines, high pollution advisors, seasonal allergy notifications, medication recalls, and the like. Moreover, in various embodiments, patient engagement module 120 can use data from care coordination module 110 and/or data analytics module 140 to create a Personal Health Record (PHR). In various embodiments, care coordination module 110 can be interfaced with the PHR to coordinate updates to the PHR based on information received from the primary, secondary, and tertiary healthcare providers.

Communication gateway module 130 can be configured to manage secure communications with a patient and providers. In accordance with various embodiments, communication gateway module 130 can be configured to communicate with patients using one or more of several different methods of communication. The secure communications can include interactive voice recognition (IVR), mobile applications, text messaging, secure email, secure portal and facsimiles, to successfully navigate patients through the ambulatory phase of care. Further, communication gateway module 130 can be configured to convert text to voice and voice to text. Interactive voice recognition can enable communication gateway module 130 to place phone calls to patients via landline and interact with patients by pushing and pulling information. Communication gateway module 130 can be capable of delivering information to patients and at the same time to recognize and covert responses to text and send the responses to the care coordinator. Secure email can enable care coordinators, providers and patients to communicate securely via email. Care coordinators can be able to deliver secure email with attachments electronically to the patients and receive replies back from the patients with attachments. The feature can also enable healthcare providers to securely communicate and share attachments. In various embodiments, communication gateway module 130 can deliver information to patients via text messaging. In one embodiment, the information delivered to patients by a text messaging will not include any protected health information. Most information delivered to patients by text messaging includes notifications and reminders. Text messaging can also be used for some instances of patient monitoring. Lastly, the mobile application can enable patients and healthcare providers to receive communication, home monitoring messages, access appointment schedules, and the like.

In various embodiments, communication gateway module 130 can transmit and receive information with the patient and healthcare providers. The care coordination system 100 can be configured to monitor the patient based on the information received from the patient and the healthcare providers. Patients who have access to the Internet or smart phones are able to log into a patient portal and access information and communicate with healthcare providers and care coordinators. In various embodiments, the patient portal allows patients access to at least one of secure communication tools, patient education, medication information, appointment scheduling request, patient registration forms, PHR and patient forums. Patients who do not have access to Internet or smart phones can communicate with care coordinators and healthcare providers through communication gateway module 130 by utilizing the voice to text functionality.

Data analytics module 140 can be configured to provide several functions throughout the care coordination and transition process. Though care coordination can be applicable to all patients in the healthcare system, care coordination can be more effective for patients with certain types of chronic illnesses. Data analytics module 140 can take into account patient risk stratification, patient risk assessment, and identifying high risk patients when determining patient candidacy. To begin the process, data analytics module 140 can be configured to analyze data to determine whether a patient is a candidate for care coordination. In various embodiments, a patient can be selected for care coordination based on the patient diagnosis. In various embodiments, care coordination system 100 may have access to electronic medical records, healthcare provider databases, or other medical or health IT applications for running a patient candidate analysis. The care coordination system can mine patient record databases for specific diagnosis medical codes. Typically an elderly person with chronic illness that will need long-term or continual care is a candidate for care coordination system 100. For example, the data on hospitals Electronic Medical Record systems can be accessed and the patient candidates can be targeted based on predetermined categories. The predetermined categories can include the previously mentioned chronic illnesses of chronic obstructive pulmonary disease (COPD), asthma, diabetes, pneumonia, congestive heart failure (CHF), and depression. These chronic illnesses consume a large portion of healthcare resources and can be more efficiently managed, thereby reducing hospital admission and readmission.

Another function provided, in various embodiments, can be data analytics module 140 configured to contribute to selection of a patient care plan, assessing the engagement and effectiveness of the patient care plan and the patient care coordination process. In various embodiments, selection of an appropriate patient care plan can be based on patient risk categories. Data analytics module 140 can also perform medication alerts and notification assessments, patient behavioral detection, automated threshold detection based on patient monitoring, patient behaviors and goals assessments, and patient surveys and data extracted from various systems. In various embodiments, data analytics module 140 can be configured to acquire patient data, analyze the patient data, and report analysis results to a built-in care coordination patient list.

In accordance with various embodiments, data analytics module 140 can also be configured to analyze changes in hospital admissions and readmissions for a healthcare provider, or a group of healthcare providers. Data analytics module 140 can assess and report the impact of care coordination system 100 on a healthcare provider's operation. Furthermore, data analytics module 140 can help track the healthcare provider's overall effectiveness on admission and readmission of patients, along with providing an avenue for measuring the impact of various changes made to the healthcare provider's operation.

Care coordination system 100 can be in communication with different entities in order to retrieve and provide information related to patient care. In various embodiments, care coordination system 100 can be in communication with a patient, healthcare providers, and medical or health information technology (IT) applications. Healthcare providers, for example, can include a care coordinator, a primary care physician (PCP), a visiting nurse, a nurse practitioner, a hospital, a physician's assistant, a therapist, a specialist, an insurance carrier, a healthcare payer, a pharmacist, an accountable care organization, a hospice provider, and the like. Similarly, medical or health IT applications, for example, can include hospital IT applications, long-term facility IT applications, accountable care organizations, HIE/EHR/EMR databases, and the like. In accordance with various embodiments, care coordination system 100 can be configured to create a virtual relationship between the healthcare providers, health IT applications, and patients on a single secure platform independent from Electronic Health Records (EHRs).

Figure 3:
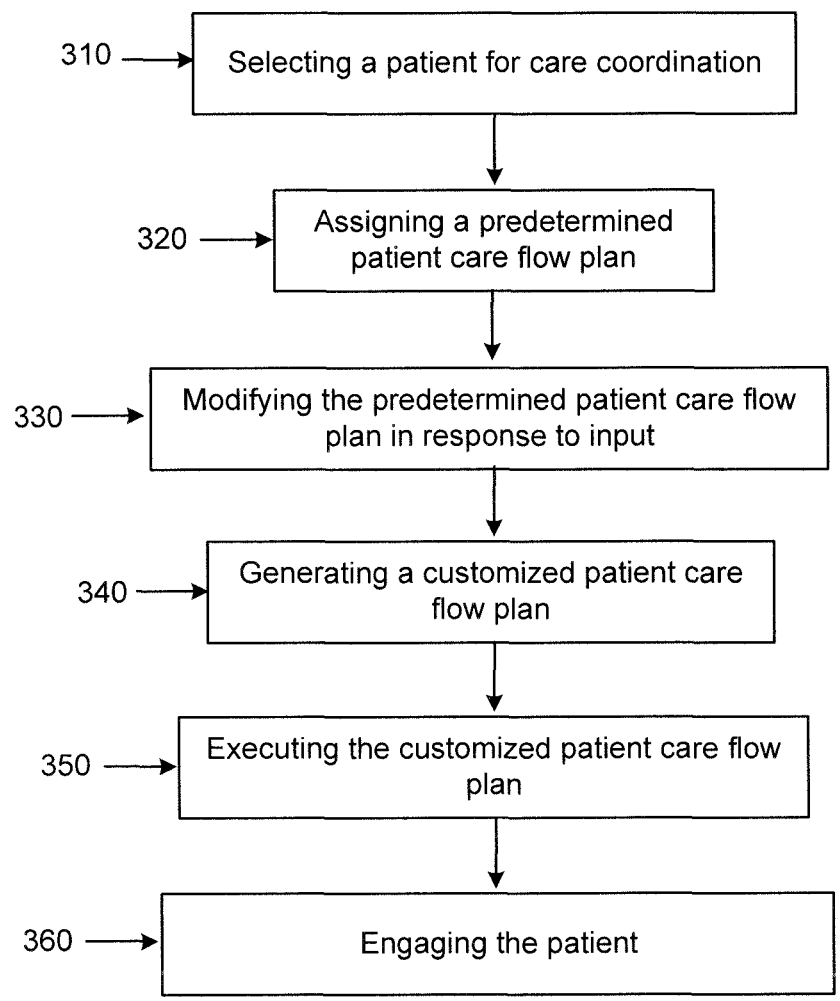
FIG. 3 illustrate a method for processing a coordinating healthcare services, in accordance with various embodiments.

In accordance with various embodiments and with reference to FIG. 3, a method of an care coordination can comprise selecting a patient for care coordination based in part on a patient diagnosis and data analytics 310, assigning a predetermined patient care flow plan to the patient based in part on the patient diagnosis 320, modifying the predetermined patient care flow plan in response to input from at least one of a healthcare provider and the patient 330, and generating a customized patient care flow plan for the patient 340, executing the customized patient care flow plan 350, and engaging the patient by providing to the patient at least one of patient scheduling, notifications, a personal health record, patient home monitoring, and patient education and medication information materials 360.

Figure 4:
FIG. 4 illustrates a screen shot of patient information related to a patient care plan, in accordance with various embodiments.

In various embodiments, a patient care flow plan for a selected patient can be created by the care coordination module 110. The patient care flow plan can be configured in the system and the system can execute the care flow plan step-by-step, while automating most steps in various embodiments. The patient care flow plan can include patient identification information, such as name, address, identification number, contact information, attending physicians and the like, as illustrated in the screenshot of FIG. 4. Further, in various embodiments, a predetermined patient care flow plan can be retrieved from a database of care flow plans, the predetermined patient care flow plan being associated with a patient diagnosis. The predetermined patient care flow plan can include a standard workflow to be implemented for the patient care based on the patient diagnosis. For example, the predetermined patient care flow plan can include information about the primary healthcare provider and supporting specialized healthcare providers based on the diagnosis information. In various embodiments, the automated predetermined patient care flow plan can coordinate the scheduling of appointments with the offices of the healthcare providers. The predetermined patient care flow plan can notify, remind, and follow-up with the patient for scheduled appointments. Further, the predetermined patient care flow plan can arrange, if needed, for transportation in various embodiments.

Figure 5:
FIG. 5 illustrates a screen shot of providing educational material, in accordance with various embodiments.

Moreover, in various embodiments, the predetermined patient care flow plan can provide medication reminders, educational material, and/or discharge summaries to the patient. In various embodiments, the care coordination system is configured to automatically send educational material to the patient based on the patient care flow plan, and can also send educational material based on patient diagnosis and treatment as illustrated in FIG. 5. For example, the patient may automatically receive informational material on a diagnosed illness and the medication prescribed for treatment. The care coordination system can also automatically send the patient discharge instructions, preparation instructions for appointments and tests and, laboratory test results.

For example, a hospital can generate its own customized patient care flow plan for specific diagnoses. The customization can be based on the hospital's capabilities, treatment option priorities, and/or own determination of best practices. By way of example and with reference to FIG. 6, a healthcare provider can generate a customized patient care flow plan by selecting specific tasks to be part of a patient care plan, and also determining the order of the selected tasks. The tasks can include such things as requesting appointments, scheduling medication reminders, scheduling patient monitoring, monitoring responses, and the like. In various embodiments, information for the patient care flow plan can be automatically uploaded from the selected patient's information from hospital admission-discharge-transfer (ADT) or EMR systems.

Figure 7A:
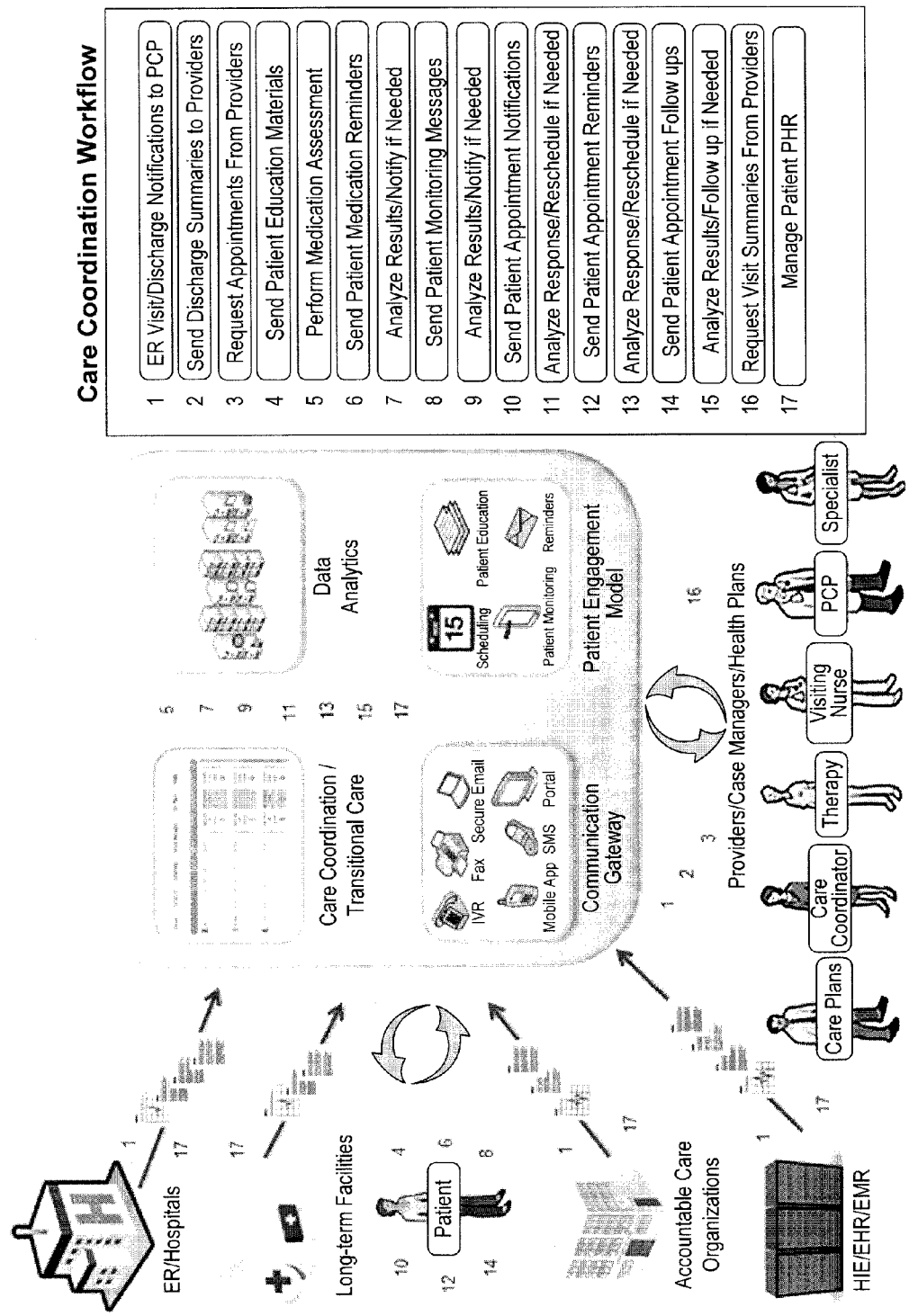

Furthermore and with continued reference to FIG. 6, the predetermined patient care flow plan can be customized to form a customized patient care flow plan. The customized patient care flow plan can include, but is not limited to: (1) patient appointment scheduling, notifications, and reminders, (2) delivery of patient education and notification, (3) patient transportation assistance, (4) medication reminders, (5) discharge summary delivery, (6) visit summary delivery, and (7) home monitoring as illustrated in the screenshot of FIG. 5. The customization can include patient preferences and institutional preferences. The customizable transitional care workflows can be modified on a patient-by-patient basis, or on a healthcare provider-by healthcare provider basis. By way of example, FIGS. 7A-7B illustrate an exemplary patient care flow plan and workflow. The illustrated workflow shows seventeen steps in the workflow, and a graphical representation of the interaction between the care coordination system, a patient, healthcare providers, and health IT applications, along with the workflow steps involving the respective parties. The various numbers surrounding the different entities in FIG. 7A correspond to the numbered steps of the workflow in FIG. 7B and are intended to illustrate the various steps of a workflow that an entity may take.

In various embodiments, a controlling healthcare provider can set its own customizations and preferences. In various embodiments, the customizable workflow process can have unique processes built and placed into the automated workflow. These unique processes may be isolated to one particular healthcare provider or copied and shared with other healthcare providers. The customized patient care flow plan can also have workflow processes removed from a basic plan if they conflict with a healthcare provider's philosophy or needs.

Moreover, a patient health record (PHR) for the selected patient can also be created by the care coordination module 110. The PHR can be part of the patient care plan or separate information. Like the patient care plan, in various embodiments, information for the PHR can be automatically uploaded from the selected patient's information from the hospital ADT or EMR systems. The PHR is separate and distinct from the patient's EMR, and the care coordination system 100 does not have control over a patient's EMR. However, like an EMR, the PHR can be HIPAA compliant. In accordance with various embodiments, access to the PHR can vary both in scope and timing. For example, different healthcare providers can have different levels of access. A primary care physician may have access to the entire PHR and may be capable of writing, editing, and reading information of the PHR. In contrast, a therapist may only be allowed access to a portion of the PHR that is relevant to the therapist services. The therapist may be allowed to write or edit only the therapist's portion of the PHR. In addition to varying scopes of access based on the healthcare provider's role, the access can also change based on timing. Specifically, in various embodiments, a healthcare provider may have access to the PHR when the patient is receiving services from that healthcare provider. For example, if a nurse practitioner is providing healthcare services to the patient for a two week period, the nurse practitioner's access can be limited to the two-week period. After the two weeks, the PHR may no longer be accessible to the nurse practitioner. However, a primary care physician may have access to the PHR at all times, regardless of whether the primary care physician is actively providing healthcare services to the patient. Furthermore, in various embodiments, a patient can be authorized to monitor all or part of the patient's PHR, and can be authorized to update a portion of the PHR. The patient updating authorization can be limited to updating the patient contact information, such as telephone number or email address.

In accordance with various embodiments, the care coordination system 100 maintains the PHR with the most recent information provided by healthcare providers. Furthermore, a patient can access his or her own PHR and provide a copy of any healthcare provider. This full access to updated information can be available during critical or traumatic illnesses, and help reduce redundancy of care or misdiagnosis, which improves care and reduces waste.

Patient engagement is an important aspect of care coordination and for improving healthcare services of selected patients. In accordance with various embodiments, care coordination system 100 can be configured to create interactive communication with patients by delivering "pushing" and asking "pulling" data. An automated system can be implemented to gather data and monitor important information about patients for healthcare providers. Care coordination system 100 can also be configured to provide patient information to the healthcare provider as needed or requested. In various embodiments, care coordination system 100 can be configured to automatically contact patients by landline, phone app, SMS or secure email to notify patients of appointments or to gather wellness information. Furthermore, care coordination system 100 can automatically send educational materials, medication reminders and information to the patients. Moreover, care coordination system 100 can automatically notify an appropriate healthcare provider in response to critical thresholds being reached. Other times, care coordination system 100 can ask patients for information regarding their care.

Furthermore, engaging the patient in the patient care plan can involve multiple actions. For example, in various embodiments, engaging the patient can comprise setting appointments on behalf of the patient with at least one healthcare provider, sending appointment notifications to the patient in response to setting the appointments, sending medication reminders to the patient, sending appointment reminders to the patient, analyzing patient responses to the medication reminders and the appointment notifications, alerting one or more healthcare providers in response to the patient responses not satisfying a predetermine criteria, providing the PHR to the healthcare provider, receiving patient visit information from the healthcare provider, and updating the PHR based on the patient visit summary. The patient visit information can include verification of the patient visit and a patient visit summary.

In various embodiments, engaging the patient in the patient care plan can further comprise requesting patient feedback of the appointment. For example, the care coordination system can contact the patient to inquire about the level of satisfaction with the visit and find out if the patient has any questions or concerns. In various embodiments, patient responses via landline or cell phone can be converted to text and sent to a care coordinator and stored in patient's PHR. Further, in various embodiments, the care coordination module can retain record of all the patient contact events.

The patient can also provide input and customization of how to be engaged with the patient care plan and care coordination. In various embodiments, the method of care coordination can include setting a patient engagement process. The patient engagement process can comprise determining appointment availability preferences of the patient, selecting an appointment notification communication preference, selecting a medication reminder communication preference, and selecting an appointment reminder communication preference. The communication preference can be one or more of the communication channel options. For example, the communication preference can be at least one of email, short message service (SMS), interactive voice response (IVR), and secure mobile messaging.

Figure 8:
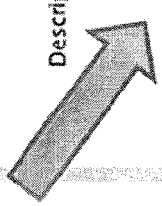
FIG. 8 illustrates a screen shot of submitting an appointment request to a healthcare provider, in accordance with various embodiments.

In accordance with various exemplary methods, the care coordination system can send appointment requests to a healthcare provider, such as the PCP or the specialist, as illustrated in the exemplary screenshot of FIG. 8. In various embodiments, the care coordination system can connect to a healthcare provider's system, determine the healthcare provider's availabilities, compare to the patient availabilities and preferences, and then send an appointment request (with one or more dates and times) to the healthcare provider. By determining and comparing the availabilities of the healthcare provider and the patient, the care coordination system is able to quickly set an appointment without the direct involvement of either party. The care coordination system can track the dates and times of the appointment requests. If an appointment request does not receive a response from the intended healthcare provider within a predetermined time, the care coordination system can send an alert to the care coordinator.

If the care coordination system receives a response to the appointment request with date and time of accepted appointments, the care coordination system can automatically update the appointment schedules for the patient and/or the healthcare provider. Moreover, care coordination system, in response to setting the appointment, and automatically set corresponding events, such as appointment reminders. The corresponding events may be set on behalf of the patient and/or on behalf of the healthcare provider.

Moreover, in various embodiments, the care coordination system can provide the PHR to the healthcare providers with scheduled appointments. The PHR can be included in an appointment request to a healthcare provider if the healthcare provider has already connected with the patient. For example, if the healthcare provider has previously provided healthcare services to the patient, the healthcare provider is granted access to the patient's PHR. In various embodiments, a patient can use the care coordination system to connect with a healthcare provider, and control which providers have access to the PHR. A care coordinator can be delegated to provide access to a PHR on the patient's behalf. In this way, a patient can control the network of providers that have access to the PHR.

Information can also be received from the patient and healthcare providers during the coordination process. In various embodiments, after a patient appointment, the care coordination system can contact the healthcare provider to verify that the schedule visit occurred and to request a copy of the visit summary. The PHR can be updated based on the information received from the healthcare provider in the visit summary. Also, the care coordination module updates the status of the appointment as completed, and determines whether the completed appointment initiates another step in the workflow process. For example, completion of an appointment may initiate the process of automatically scheduling a follow-up appointment.

Figure 9:
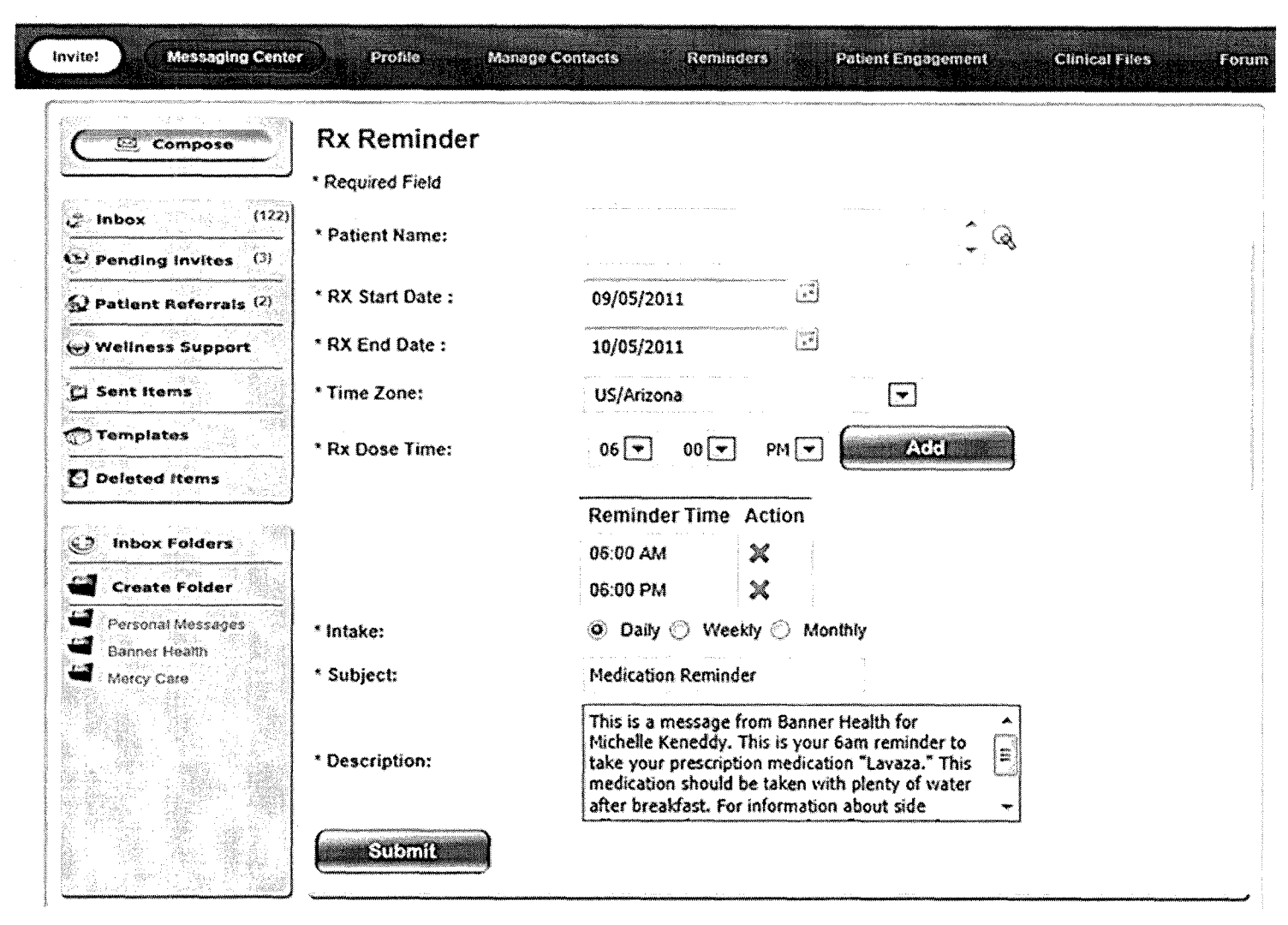
Figure 10:
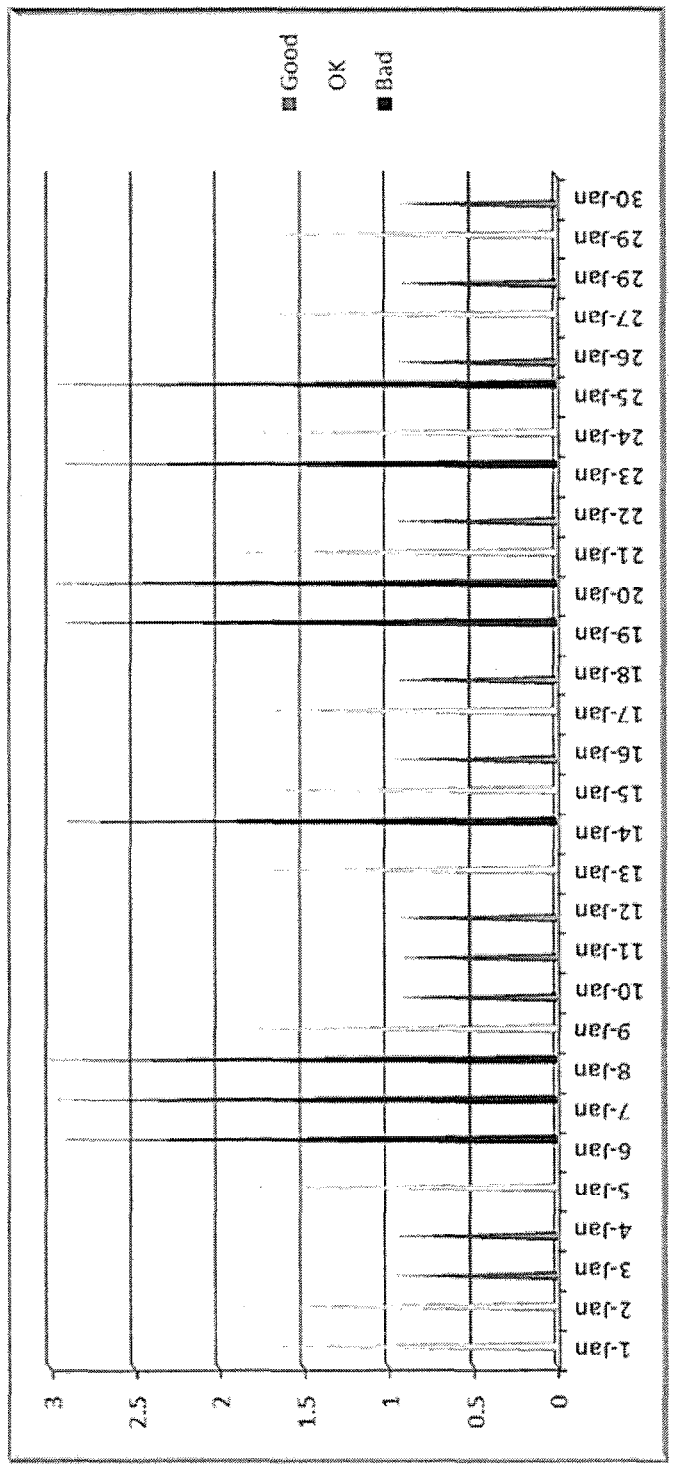
FIG. 10 illustrates a screen shot of patient feedback analysis, in accordance with various embodiments.
Figure 11:
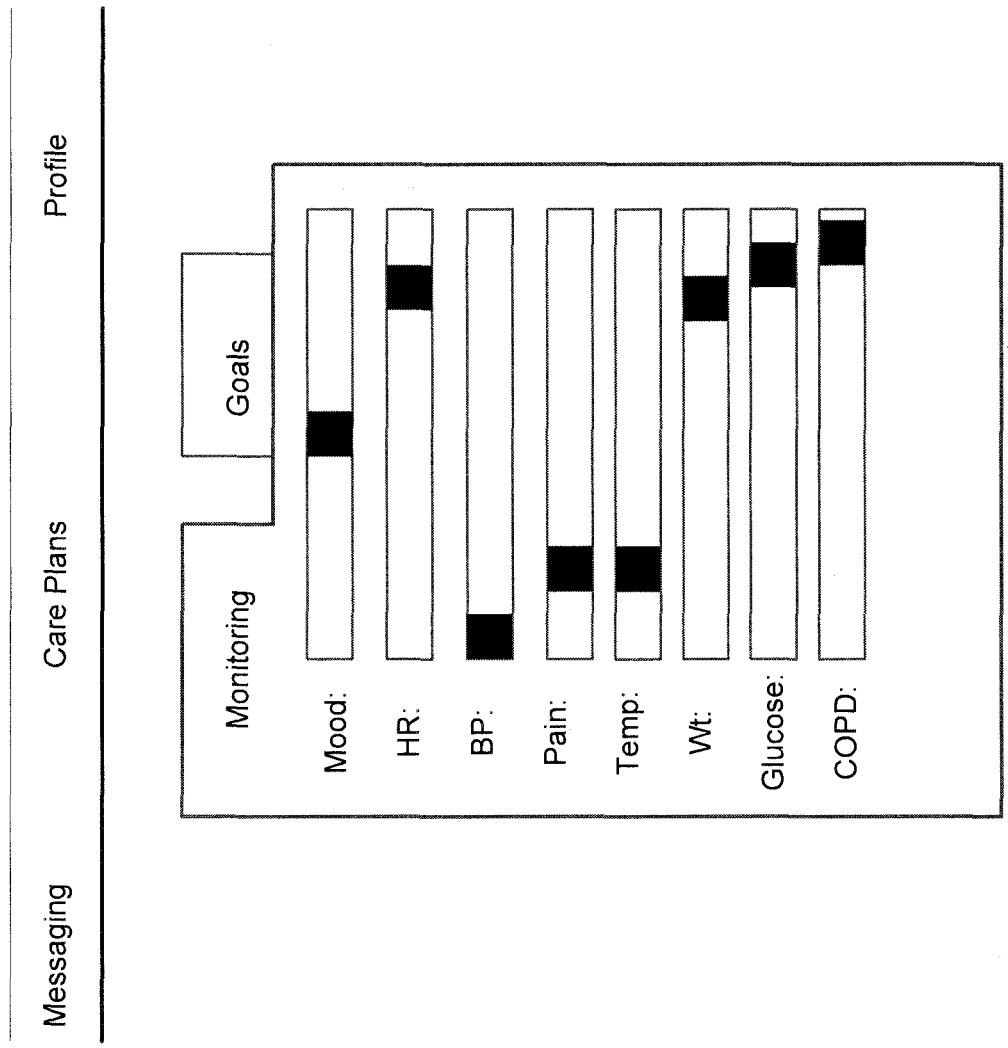
FIG. 11 illustrates a screen shot of patient monitoring display, in accordance with various embodiments.

During the coordination process, it is important to monitor and assess whether the patient is engaged in the patient care plan. One method of monitoring is creating a home monitoring campaign. In various embodiments, the home monitoring campaign can enable the care coordination system to send monitoring messages to the patients while extracting and analyzing results. These messages can include the appointment reminders, medication reminders, and follow-up questions that are sent to the patient. The medication reminders can include a prescription start date and end date, the time the medication should be administered, and may include instructions for taking the medication, as illustrated in the exemplary screenshot of FIG. 9. In accordance with various embodiments, the home monitoring campaign system not only sends medication reminders to patients but it also asks patients to respond as to whether they will be able to take the medication or not. The care coordination system also provides medication information to patients and allows patients to ask for additional information. The care coordinator can be alerted if the patient is unable to take medication, does not respond to medication reminders or has questions regarding to the medication. Furthermore, in various embodiments, the home monitoring campaign can also include generating automatic daily patient monitoring messages via SMS, landline, phone application, or other communication channels. As an example, the patient monitoring messages can ask a patient to rate his or her pain for the day. The care coordination system can be configured to receive the patient response, analyze the response based on predetermined thresholds, and notify a care coordinator or healthcare provider if the pain numbers exceed a threshold. In various embodiments, the patient pain response can be charted for quick review by a care coordinator, as illustrated in the exemplary screenshot of FIG. 10. In addition to pain, the care coordination system can also monitor, and provide a dashboard summary of, a patient's general health indicators, such as mood, heart rate, blood pressure, pain level, temperature, weight, and the like as illustrated in the screenshot in FIG. 11.

In accordance with various embodiments, the care coordination system can further comprise a medication reconciliation module. The medication reconciliation module can be configured to manage a patient medication list and reconcile modifications. In various embodiments, the medication reconciliation module can update the patient's medication list, manage patient medication, and generate alerts and notifications based on prescription changes. Moreover, the medication reconciliation module can add, remove, or modify existing medication items in patient's medication list. The medication reconciliation module can retrieve medication information from a patient, healthcare providers, and medical or health information technology (IT) applications.

In accordance with various embodiments, the care coordination system can transition management or control of the patient care plan to different healthcare providers at various times. The control transfer can be similar to the changing PHR access described above using an authorization module. In other words, a first healthcare provider can control the patient care plan and all the associated aspects for a first period of time, and then control can be transferred to a second healthcare provider. By way of example, a hospital can have initial control and development of a patient care plan while the patient has been recently treated by the hospital. After a determined timeframe has passed, for example 30 days, control of the patient care plan can transfer to a therapist that is currently treating the patient. In another example, management of the patient care plan can be transferred between hospitals if the patient care is also being transferred between hospitals. Furthermore, in various embodiments, a first healthcare provider can be authorized to control the patient care plan even while the patient is receiving health services from multiple healthcare providers. In other words, authorization to control the patient care plan does not automatically transfer to each healthcare provider that is currently servicing the patient.

In various embodiments, the care coordination system can manage care transition in a different model, namely providing control to multiple healthcare providers concurrently. Transition of care can include, but is not limited to, providing authorization to set appointments, manage medication reminders and notifications, updating the PHR, notifying other healthcare providers of patient updates, and the like.

During the coordination process, control of the patient care flow plan can be transferred to a second healthcare provider. For example, control can be transferred from a hospital care coordinator to a PCP care coordinator. All the patient information that was available to the hospital care coordinator can be available to the PCP care coordinator. In various embodiments, care coordination system can generate a summary report of healthcare provided by the first healthcare provider (the hospital in this example). The summary report can be submitted to the patient's EMR in the EMR system. The summary report can also be inserted into the patient's PHR on the care coordination system.

After control is transferred to the second healthcare provider, the second healthcare provider can continue navigating the patient through the coordination process by providing the patient with information, monitoring, appointments, and the like. In accordance with various embodiments, the second healthcare provider can be responsible for providing the same functions as the first healthcare provider. The second healthcare provider can continue to inform and engage the patient in the care process, and share the PHR among treating healthcare providers.

In various embodiments, the care coordination system can also collect and analyze data to predict potential health problems before becoming acute. The care coordination system can be configured to contact a patient's healthcare providers, such as PCPs, of potential issues in order to coordination health services earlier in the process. The earlier services should prevent hospital admissions and readmissions. For example, the care coordination system can be configured to track whether or not patients are making their scheduled appointments, pain levels, and taking the prescribed medication. Follow up care is important in preventing readmissions, and missed appointments can be relayed to ambulatory care coordinators so that they can intervene before readmissions occur.

Data analytics module 140 can include outcome analysis capabilities. By way of example only, an evaluation of the care coordination system can be achieved using the following workflow. In various embodiments, care coordination system can create a single repository of data warehousing system with data from three possible sources: a care coordination system, hospital EHR systems and CMS claim processing systems. The data analytics engine can measure the level of patient involvement, care coordination workflow, PCP and specialist participation, and flow of data. Furthermore, the care coordination system can measure results by performing data mining and data analytics utilizing admission and discharge data from the hospitals. Care coordination system can measure results by performing data mining and data analysis utilizing CMS hospital claim data. The data in its entirety can be analyzed and results can be reported. In various embodiments, process improvements can be determined based on the results.

Figure 12:
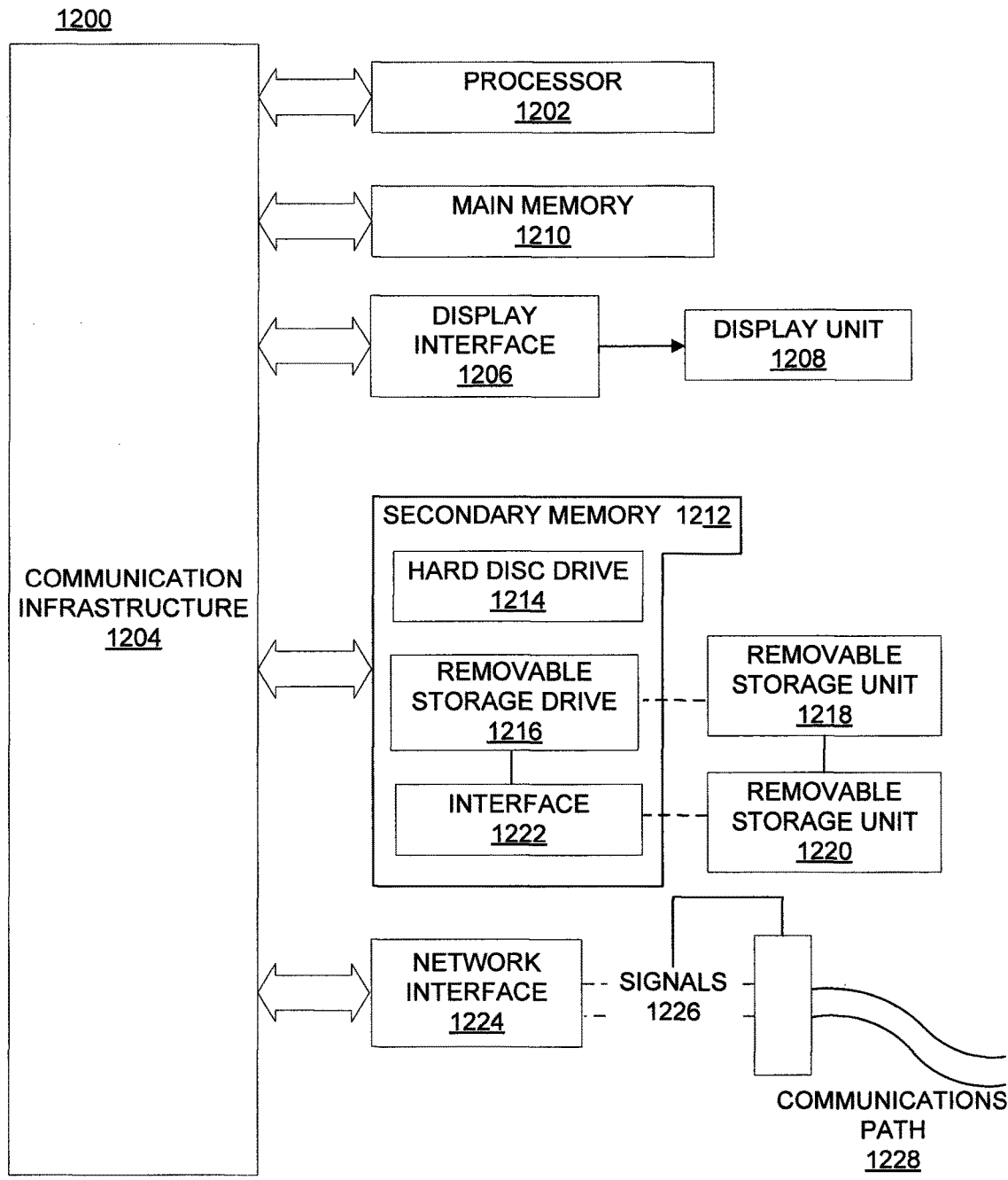
FIG. 12 illustrates a block diagram of a computer system for implementing the present disclosure, in accordance with various embodiments.

In accordance with various embodiments, the present disclosure is directed towards one or more computer systems capable of carrying out the functionality described herein. An example of the computer systems includes a computer system 1200, which is shown in FIG. 12. The computer system 1200 includes at least one processor, such as a processor 1202. Processor 1202 is connected to a communication infrastructure 1204, for example, a communications bus, a cross over bar, a network, and the like. Various software embodiments are described in terms of this exemplary computer system 1200. After reading this description, it will become apparent to a person skilled in the relevant art(s) how to implement the present disclosure using other computer systems and/or architectures.

The computer system 1200 includes a display interface 1206 that forwards graphics, text, and other data from the communication infrastructure 1204 (or from a frame buffer which is not shown in FIG. 12) for display on a display unit 1208. The computer system 1200 further includes a main memory 1210, such as random access memory (RAM), and may also include a secondary memory 1212. The secondary memory 1212 may further include, for example, a hard disk drive 1214 and/or a removable storage drive 1216, representing a floppy disk drive, a magnetic tape drive, an optical disk drive, etc. The removable storage drive 1216 reads from and/or writes to a removable storage unit 1218 in a well-known manner. The removable storage unit 1218 may represent a floppy disk, magnetic tape or an optical disk, and may be read by and written on by the removable storage drive 1216. As will be appreciated, the removable storage unit 1218 includes a computer usable storage medium having stored therein, computer software and/or data.

In accordance with various embodiments of the present disclosure, the secondary memory 1212 may include other similar devices for allowing computer programs or other instructions to be loaded into the computer system 1200. Such devices may include, for example, a removable storage unit 1220, and an interface 1222. Examples of such devices may include a program cartridge and cartridge interface (such as that found in video game devices), a removable memory chip (such as an erasable programmable read only memory (EPROM), or programmable read only memory (PROM)) and associated socket, and other removable storage units 1220 and interfaces 1222, which allow software and data to be transferred from the removable storage unit 1220 to the computer system 1200.

The computer system 1200 may further include a communication interface 1224. The communication interface 1224 allows software and data to be transferred between the computer system 1200 and external devices. Examples of the communication interface 1224 include, but may not be limited to a modem, a network interface (such as an Ethernet card), a communications port, a Personal Computer Memory Card International Association (PCMCIA) slot and card, and the like. Software and data transferred via the communication interface 1224 are in the form of a plurality of signals, hereinafter referred to as signals 1226, which may be electronic, electromagnetic, optical or other signals capable of being received by the communication interface 1224. The signals 1226 are provided to the communication interface 1224 via a communication path (e.g., channel) 1228. The communication path 1228 carries the signals 1226 and may be implemented using wire or cable, fiber optics, a telephone line, a cellular link, a radio frequency (RF) link and other communication channels.

In this document, the terms "computer program medium" and "computer usable medium" are used to generally refer to media such as the removable storage drive 1216, a hard disk installed in hard disk drive 1214, the signals 1226, and the like. These computer program products provide software to the computer system 1200. The present disclosure is directed to such computer program products.

Computer programs (also referred to as computer control logic) are stored in the main memory 1210 and/or the secondary memory 1212. Computer programs may also be received via the communication interface 1224. Such computer programs, when executed, enable the computer system 1200 to perform the features of the present disclosure, as discussed herein. In particular, the computer programs, when executed, enable the processor 1202 to perform the features of the present disclosure. Accordingly, such computer programs represent controllers of the computer system 1200.

In various embodiments, where the present disclosure is implemented using a software, the software may be stored in a computer program product and loaded into the computer system 1200 using the removable storage drive 1216, the hard disk drive 1214 or the communication interface 1224. The control logic (software), when executed by the processor 1202, causes the processor 1202 to perform the functions of the present disclosure as described herein.

In various embodiments, the present disclosure is implemented primarily in hardware using, for example, hardware components such as application specific integrated circuits (ASIC). Implementation of the hardware state machine so as to perform the functions described herein will be apparent to persons skilled in the relevant art(s).

In yet another embodiment, the present disclosure is implemented using a combination of both the hardware and the software.

The various embodiments of the present disclosure have been described above, it should be understood that they have been presented by way of example, and not limitation. It will be apparent to persons skilled in the relevant art(s) that various changes in form and detail can be made therein without departing from the spirit and scope of the present disclosure. Thus, the present disclosure should not be limited by any of the above described exemplary embodiments, but should be defined only in accordance with the following claims and their equivalents.

In addition, it should be understood that the figures illustrated in the attachments, which highlight the functionality and advantages of the present disclosure, are presented for example purposes only. The architecture of the present disclosure is sufficiently flexible and configurable, such that it may be utilized (and navigated) in ways other than that shown in the accompanying figures. Systems, methods and computer program products are provided.

In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic.

Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Any communication, transmission and/or channel discussed herein may include any system or method for delivering content (e.g. data, information, metadata, etc), and/or the content itself. The content may be presented in any form or medium, and in various embodiments, the content may be delivered electronically and/or capable of being presented electronically. For example, a channel may comprise a website or device (e.g., Facebook, YouTube, AppleTV, Pandora, xBox, Sony Playstation), a uniform resource locator ("URL"), a document (e.g., a Microsoft Word document, a Microsoft Excel document, an Adobe .pdf document, etc.), an "ebook," an "emagazine," an application or microapplication (as described herein), an SMS or other type of text message, an email, facebook, twitter, MMS and/or other type of communication technology. In various embodiments, a channel may be hosted or provided by a data partner. In various embodiments, the distribution channel and/or the may comprise at least one of a merchant website, a social media website, affiliate or partner websites, an external vendor, a mobile device communication, social media network and/or location based service. Distribution channels may include at least one of a merchant website, a social media site, affiliate or partner websites, an external vendor, and a mobile device communication. Examples of social media sites include Facebook®, Foursquare®, Twitter®, MySpace®, LinkedIn®, and the like. Examples of affiliate or partner websites include American Express®, Groupon®, LivingSocial®, and the like. Moreover, examples of mobile device communications include texting, email, and mobile applications for smartphones. In various embodiments, the server may include application servers (e.g. WEB SPHERE, WEB LOGIC, JBOSS). In various embodiments, the server may include web servers (e.g. APACHE, IIS, GWS, SUN JAVA SYSTEM WEB SERVER).

A web client includes any device (e.g., personal computer) which communicates via any network, for example such as those discussed herein. Such browser applications comprise Internet browsing software installed within a computing unit or a system to conduct online transactions and/or communications. These computing units or systems may take the form of a computer or set of computers, although other types of computing units or systems may be used, including laptops, notebooks, tablets, hand held computers, personal digital assistants, set-top boxes, workstations, computer-servers, main frame computers, mini-computers, PC servers, pervasive computers, network sets of computers, personal computers, such as iPads, iMACs, and MacBooks, kiosks, terminals, point of sale (POS) devices and/or terminals, televisions, or any other device capable of receiving data over a network. A web-client may run Microsoft Internet Explorer, Mozilla Firefox, Google Chrome, Apple Safari, or any other of the myriad software packages available for browsing the internet.

Practitioners will appreciate that a web client may or may not be in direct contact with an application server. For example, a web client may access the services of an application server through another server and/or hardware component, which may have a direct or indirect connection to an Internet server. For example, a web client may communicate with an application server via a load balancer. In an exemplary embodiment, access is through a network or the Internet through a commercially-available web-browser software package.

As those skilled in the art will appreciate, a web client includes an operating system (e.g., Windows NT, 95/98/2000/CE/Mobile, OS2, UNIX, Linux, Solaris, MacOS, PalmOS, etc.) as well as various conventional support software and drivers typically associated with computers. A web client may include any suitable personal computer, network computer, workstation, personal digital assistant, cellular phone, smart phone, minicomputer, mainframe or the like. A web client can be in a home or business environment with access to a network. In an exemplary embodiment, access is through a network or the Internet through a commercially available web-browser software package. A web client may implement security protocols such as Secure Sockets Layer (SSL) and Transport Layer Security (TLS). A web client may implement several application layer protocols including http, https, ftp, and sftp.

In various embodiments, components, modules, and/or engines of system 100 may be implemented as micro-applications or micro-apps. Micro-apps are typically deployed in the context of a mobile operating system, including for example, a Palm mobile operating system, a Windows mobile operating system, an Android Operating System, Apple iOS, a Blackberry operating system and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

As used herein, the term "network" includes any cloud, cloud computing system or electronic communications system or method which incorporates hardware and/or software components. Communication among the parties may be accomplished through any suitable communication channels, such as, for example, a telephone network, an extranet, an intranet, Internet, point of interaction device (point of sale device, personal digital assistant (e.g., iPhone®, Palm Pilot®, Android®, Blackberry®), cellular phone, kiosk, etc.), online communications, satellite communications, off-line communications, wireless communications, transponder communications, local area network (LAN), wide area network (WAN), virtual private network (VPN), networked or linked devices, keyboard, mouse and/or any suitable communication or data input modality. Moreover, although the system is frequently described herein as being implemented with TCP/IP communications protocols, the system may also be implemented using IPX, Appletalk, IP-6, NetBIOS, OSI, any tunneling protocol (e.g. IPsec, SSH), or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art and, as such, need not be detailed herein. See, for example, Dilip Naik, Internet Standards and Protocols (1998); Java 2 Complete, various authors, (Sybex 1999); Deborah Ray and Eric Ray, Mastering HTML 4.0 (1997); and Loshin, TCP/IP Clearly Explained (1997) and David Gourley and Brian Totty, HTTP, The Definitive Guide (2002), the contents of which are hereby incorporated by reference.

The various system components may be independently, separately or collectively suitably coupled to the network via data links which includes, for example, a connection to an Internet Service Provider (ISP) over the local loop as is typically used in connection with standard modem communication, cable modem, Dish networks, ISDN, Digital Subscriber Line (DSL), or various wireless communication methods, see, e.g., Gilbert Held, Understanding Data Communications (1996), which is hereby incorporated by reference. It is noted that the network may be implemented as other types of networks, such as an interactive television (ITV) network. Moreover, the system contemplates the use, sale or distribution of any goods, services or information over any network having similar functionality described herein.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand. For more information regarding cloud computing, see the NIST's (National Institute of Standards and Technology) definition of cloud computing at http://csrc.nist.gov/publications/nistpubs/800-145/SP800-145.pdf (last visited June 2012), which is hereby incorporated by reference in its entirety.

Any databases discussed herein may include relational, hierarchical, graphical, or object-oriented structure and/or any other database configurations. Common database products that may be used to implement the databases include DB2 by IBM (Armonk, N.Y.), various database products available from Oracle Corporation (Redwood Shores, Calif.), Microsoft Access or Microsoft SQL Server by Microsoft Corporation (Redmond, Wash.), MySQL by MySQL AB (Uppsala, Sweden), or any other suitable database product. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

What is claimed is:

1. A method of care coordination, the method comprising:
    selecting, by an electronic, computer-based care coordination system, a patient for care coordination based in part on a patient diagnosis and data analytics;
    assigning, by the care coordination system and to the patient, a predetermined patient care flow plan selected from a plurality of predetermined patient care flow plans, based in part on the patient diagnosis, the predetermined patient care flow plan comprising a plurality of steps;
    modifying, by the care coordination system, the predetermined patient care flow plan in response to input from at least one of a healthcare provider or the patient in order to generate a customized patient care flow plan for the patient, wherein the care coordination system comprises a database, and wherein the modifying, by the care coordination system, the predetermined patient care flow plan comprises:
        (a) tuning, by the care coordination system, the database to optimize database performance, wherein the tuning includes placing frequently used files as indexes on separate file systems to reduce in and out bottlenecks;
        (b) designating, by the care coordination system, a key field in data tables to speed searching for the predetermined patient care flow plan; and
        (c) sorting, by the care coordination system, the plurality of predetermined patient care flow plans according to a known order to simplify the lookup process; and
    engaging the patient in the customized patient care flow plan, wherein the engaging the patient in the customized patient care flow plan comprises providing to the patient at least one of patient medical appointment scheduling, notifications, a personal health record, patient home monitoring, or patient education and medication information materials, and wherein the engaging the patient in the customized patient care flow plan further comprises, by the care coordination system:
        (d) setting appointments on behalf of the patient with the healthcare provider;
        (e) sending appointment notifications to the patient in response to setting the appointments;
        (f) sending medication reminders to the patient;
        (g) sending appointment reminders to the patient;
        (h) analyzing patient responses to the medication reminders and the appointment notifications;
        (i) alerting the healthcare provider in response to the patient responses not satisfying a predetermined criteria;
        (j) providing the customized patient care flow plan to the healthcare provider;
        (k) receiving patient visit information from the healthcare provider, wherein the patient visit information includes verification of a patient visit and a patient visit summary; and
        (l) updating the customized patient care flow plan based on the patient visit information.

2. The method of claim 1, further comprising updating, by the care coordination system, the customized patient care flow plan based on updated patient information and treatment.

3. The method of claim 1, wherein the care coordination system is configured to communicate using multiple communication methods.

4. The method of claim 1, further comprising transitioning authorization control of the customized patient care flow plan from a first healthcare provider to a second healthcare provider for care coordination.

5. The method of claim 4, wherein the care coordination system is configured to communicate with multiple healthcare providers, and wherein the multiple healthcare providers include at least one of a care coordinator, a primary care physician (PCP), a visiting nurse, a nurse practitioner, a hospital, a physician's assistant, a therapist, a specialist, an insurance carrier, a healthcare payer, a pharmacist, an accountable care organization, or a hospice provider.

6. The method of claim 1, wherein the engaging the patient in the customized patient care flow plan further comprises requesting patient feedback of the patient visit.

7. The method of claim 1, further comprising setting a patient engagement process, wherein the patient engagement process comprises:
   determining appointment availability preferences of the patient;
   selecting an appointment notification communication preference;
   selecting a medication reminder communication preference; and
   selecting an appointment reminder communication preference;
   wherein a communication preference is at least one of secure email, facsimile, short message service (SMS), interactive voice response (IVR), or secure mobile messaging.

8. The method of claim 1, further comprising generating, by the care coordination system, a patient health record (PHR) of the patient, wherein the generating the PHR comprises compiling patient information from at least one of an electronic medical record (EMR) system, an admission-discharge-transfer system, or a care provider system.

9. The method of claim 8, wherein the patient can monitor and update at least a portion of the PHR.

10. The method of claim 9, wherein the care coordination system is configured to control an access level to the PHR based on a type of healthcare provider, and wherein an update to the PHR is also updated in an electronic medical record of the patient.

11. The method of claim 1, wherein the healthcare provider is at least one of a care coordinator, a primary care physician (PCP), a visiting nurse, a nurse practitioner, a hospital, a physician's assistant, a therapist, a specialist, an insurance carrier, a healthcare payer, a pharmacist, an accountable care organization, or a hospice provider.

12. The method of claim 1, wherein the care coordination system comprises a data analytics module that performs at least one of patient behavioral detection, selection of a patient care plan based on patient risk categories, or analyze changes in hospital admissions and readmissions for a health care provider.

* * * * *